United States Patent
Callisen et al.

(10) Patent No.: US 7,282,233 B2
(45) Date of Patent: Oct. 16, 2007

(54) CHEMICALLY MODIFIED LIPOLYTIC ENZYME

(75) Inventors: Thomas Honger Callisen, Frederiksberg C (DK); Shamkant Anant Patkar, Lyngby (DK); Allan Svendsen, Birkerod (DK); Jesper Vind, Lyngby (DK)

(73) Assignee: Novozymes A/S, Bagsvaerd (DK)

( * ) Notice: Subject to any disclaimer, the term of this patent is extended or adjusted under 35 U.S.C. 154(b) by 222 days.

(21) Appl. No.: 11/214,188

(22) Filed: Aug. 29, 2005

(65) Prior Publication Data

US 2005/0281912 A1 Dec. 22, 2005

Related U.S. Application Data

(62) Division of application No. 10/019,156, filed as application No. PCT/DK00/00300 on Jun. 2, 2000, now Pat. No. 6,964,944.

(60) Provisional application No. 60/138,081, filed on Jun. 8, 1999.

(30) Foreign Application Priority Data

Jun. 2, 1999 (DK) ................................ 1999 00778

(51) Int. Cl.
*A21D 10/00* (2006.01)

(52) U.S. Cl. ....................................... 426/549; 435/198
(58) Field of Classification Search .................... None
See application file for complete search history.

(56) References Cited

FOREIGN PATENT DOCUMENTS

| EP | 0 258 068 | 3/1988 |
|---|---|---|
| EP | 0 305 216 | 3/1989 |
| WO | WO92/05249 | 4/1992 |
| WO | WO94/04035 | 3/1994 |
| WO | WO94/14963 | 7/1994 |
| WO | WO95/35381 | 12/1995 |
| WO | WO98/26057 | 5/1998 |

OTHER PUBLICATIONS

Green et al., JAOCS, vol. 75, No. 11, pp. 1519-1526 (1998).
Murakami et al., JAOCS, vol. 70, No. 6, pp. 571-574 (Jun. 1993).
Takahashi et al., Biosci. Biotech. Biochem., 59 (5), pp. 809-812, (1995).
Binsbergen et al., Peptides pp. 666-669 (1998).
Plou et al., Stability and Stabilization of Biocatalysis; pp. 115-120 (1998).

*Primary Examiner*—Nashaat T. Nashed
(74) *Attorney, Agent, or Firm*—Jason I. Garbell

(57) ABSTRACT

Lipolytic enzymes are chemically modified by covalently linking one or more (particularly 1-3) hydrophobic groups to the enzyme molecule. The chemical modification improves the performance of the lipolytic enzyme, e.g., in baking or in detergents.

12 Claims, No Drawings

CHEMICALLY MODIFIED LIPOLYTIC ENZYME

CROSS-REFERENCE TO RELATED APPLICATIONS

This application is a division of U.S. application Ser. No. 10/019,156, filed Dec. 3, 2001, which is a 35 U.S.C. 371 national application of PCT/DK00/00300 filed Jun. 2, 2000 (the international application was published under PCT Article 21(2) in English) and claims, under 35 U.S.C. 119, priority of Danish application no. PA 1999 00778 filed Jun. 2, 1999 and the benefit of U.S. provisional application no. 60/138,081 filed Aug. 6, 1999, the contents of which are fully incorporated herein by reference.

FIELD OF THE INVENTION

The present invention relates to a chemically modified lipolytic enzyme, its preparation and its to uses thereof.

BACKGROUND OF THE INVENTION

Lipolytic enzymes such as lipases and phospholipases are used, e.g., in detergents and baking.

Thus, lipases have been used for a number of years as detergent enzymes to remove lipid or fatty stains from clothes and other textiles, particularly a lipase derived from *Humicola lanuginosa* (EP 258 068 and EP 305 216) sold under the trade name Lipolase® (product of Novo Nordisk A/S).

Fatty acid-modified lipases and their use in transesterification have been described. M. Murakami et al., JAOCS, 70 (6), 571-574 (1993); K. Green et al., JAOCS, 75 (11), 1519-1526 (1998).

It is also known to add lipases and phospholipases to breadmaking dough. WO 94/04035; WO 98/26057.

SUMMARY OF THE INVENTION

The inventors have developed lipolytic enzymes which are chemically modified by covalently linking one or more hydrophobic groups to the enzyme molecule. They found that the chemical modification may improve the performance of the lipolytic enzyme, e.g., in baking or in detergents. The benefits may include improved thermostability and an altered substrate specificity. A modified lipase or cutinase may show improved detergency, particularly improved first-wash performance, whiteness maintenance, dingy cleanup, and reduced formation of fatty acids during the drying process with less risk of forming an unpleasant smell. The benefits in baking include an increased loaf volume.

Accordingly, the invention provides a lipolytic enzyme which is chemically modified by having one or more (particularly 1-3) hydrophobic groups covalently linked to the enzyme. The invention also provides us of such modified lipolytic enzyme in detergents and baking.

The invention further provides a method of preparing a chemically modified lipolytic enzyme by covalently linking hydrophobic groups to a parent lipolytic enzyme. Optionally, the amino acid sequence of the enzyme may be modified before the covalent linking.

DETAILED DESCRIPTION OF THE INVENTION

Parent Lipolytic Enzyme

The lipolytic enzyme is an enzyme classified under the Enzyme Classification number E.C. 3.1.1.—(Carboxylic Ester Hydrolases) in accordance with the Recommendations (1992) of the International Union of Biochemistry and Molecular Biology (IUBMB). Thus, the lipolytic enzyme may exhibit hydrolytic activity, typically at a water/lipid interface, towards carboxylic ester bonds in substrates such as mono-, di- and triglycerides, phospholipids, thioesters, cholesterol esters, wax-esters, cutin, suberin, synthetic esters or other lipids mentioned in the context of E.C. 3.1.1. The lipolytic enzyme may, e.g., have activity lipase activity (with triglycerides as substrate), phospholipase activity, esterase activity or cutinase activity.

The parent lipolytic enzyme may be prokaryotic, particularly a bacterial enzyme, e.g. from *Pseudomonas*. Examples are *Pseudomonas* lipases, e.g. from *P. cepacia, P. glumae, P. pseudoalcaligenes* and *Pseudomonas* sp. strain SD 705. Other examples are bacterial cutinases, e.g. from *Pseudomonas* such as *P. mendocina* (U.S. Pat. No. 5,389,536) or *P. putida* (WO 88/09367).

Alternatively, the parent lipolytic enzyme may be eukaryotic, e.g. fungal, such as lipolytic enzymes of the Humicola family and the *Zygomycetes* family and fungal cutinases. Examples of fungal cutinases are the cutinases of *Fusarium solani pisi* and *Humicola insolens*.

The Humicola family of lipolytic enzymes consists of the lipase from *H. lanuginosa* strain DSM 4109 and lipases having more than 50% homology with said lipase. The lipase from *H. lanuginosa* (synonym *Thermomyces lanuginosus*) is described in EP 258 068 and EP 305 216, and has the amino acid sequence shown in positions 1-269 of SEQ ID NO: 2 of U.S. Pat. No. 5,869,438.

The Humicola family also includes the following lipolytic enzymes: lipase from *Penicillium camembertdi*, lipase/phospholipase from *Fusarium oxysporum*, lipase from *F. heterosporum*, lysophospholipase from *Aspergillus foetidus*, phospholipase A1 from *A. oryzae*, lipase from *A. oryzae*, lipase/ferulic acid esterase from *A. niger*, lipase/ferulic acid esterase from *A. tubingensis*, lipase from *A. tubingensis*, lysophospholipase from *A. niger* and lipase from *F. solani*.

The Zygomycetes family comprises lipases having at least 50% homology with the lipase of *Rhizomucor miehei*. This family also includes the lipases from *Absidia reflexa, A. sporophora, A. corymbifera, A. blakesleeana, A. griseola* and *Rhizopus oryzae*.

The phospholipase may have $A_1$ or $A_2$ activity to remove fatty acid from the phospholipid and form a lyso-phospholipid, or it may be have phospholipase B or lysophospholipase activity. It may or may not have lipase activity, i.e. activity on triglycerides. The phospholipase may be of animal origin, e.g. from pancreas (e.g. bovine or porcine pancreas), snake venom or bee venom. Alternatively, the phospholipase may be of microbial origin, e.g. from filamentous fungi, yeast or bacteria, such as the genus *Aspergillus, Fusarium* or *Hyphozyma* (WO 98/18912), particularly the species *A. niger* or *F. oxysporum* (WO 98/26057).

Other examples of lipolytic enzymes are described in PCT/DK 99/00664 (Danish patent application PA 1998 01572).

The lipolytic enzyme may be native to such source, or it may be a variant thereof obtained by altering the amino acid sequence. Examples of such variants are those described in WO 92/05249, WO 94/25577, WO 95/22615, WO 97/04079 and WO 97/07202, WO 98/08939, PCT/DK 99/00068, EP 99610010.3 and Danish patent application PCT/DK 00/00156 (PA 1999 00441). A specific example is a variant of the *Humicola lanuginosa* lipase having the mutations E1SPPCGRRP+E99N+N101S+E239C+Q249R.

Hydrophobic Group

Generally, a hydrophobic group can be identified from a negative free-energy-of-transfer from water to oil. More specifically, suitable hydrophobic groups can be identified in a partition coefficient experiment where the two media are an aqueous detergent solution and a surface containing the (lipid) substrate of choice. The general concept is described in standard text books such as C. Tanford (1980), The hydrophobic effect, Wiley, N.Y.

The hydrophobic group may be a fatty acyl group, particularly having 12-22 or 14-20 carbon atoms, straight-chain or branched, saturated, mono- or polyunsaturated, optionally substituted. Examples are myristoyl (tetradecanoyl), palmitoyl (hexadecanoyl), stearoyl (octadecanoyl) and arachidoyl (eicosanoyl).

Other examples of hydrophobic groups are those commonly found in surfactants, e.g. a hydrophobic polymer group such as poly-alkoxy or alkyl-polyalkoxy of the general formula $R^1-(O-CHR^2-CH_2)_n$ wherein $R^1$ is H or $C_{14}-C_{22}$ alkyl, $R^2$ is H or methyl, and n is 10-200, e.g. 20-100.

The hydrophobic group(s) may particularly be linked to an amino acid in the lipid contact zone of the lipolytic enzyme (as described in WO 92/05249) or within 5 Å from the edge of said zone.

The modified lipolytic enzyme containing one, two or three hydrophobic groups will be referred to as a monopod, dipod or tripod, respectively.

Covalent Linking

The hydrophobic group may be covalently linked, e.g., to an amino group (lysine or N-terminal), a thiol group (cysteine residues), a hydroxyl group (serine or threonine) or a carboxyl group (glutamic acid, aspartic acid or C-terminal) in the amino acid sequence of the lipolytic enzyme. The covalent linking can be done by methods known in the art.

Thus, linking to amino groups can be done through a reactive intermediate such as an N-hydroxy-succinimide activated fatty acids, e.g. stearoyl or arachidoyl acid N-hydroxy-succinimide, or maleimide esters at high pH (e.g. pH 8-9).

Linking to a thiol group can be done by linking to a maleimide ester at pH 6.5-7, by reaction with fatty acid methane thiosulfonate (e.g. at pH 8), or as described in |WO 91/16423|, |WO 98/23732 or WO 99/3732|.

Linking to a carboxyl group can be done by linking a hydrophobic amine as described in |WO 95/09909|.

To ensure that the number of hydrophobic groups linked to each enzyme molecule will be from one to three, one strategy uses a lipolytic enzyme having an amino acid sequence with one, two or three of the group in question (e.g. amino or thiol). This is discussed below.

Another strategy is to choose the conditions (amounts of reagents etc.) for the linking reaction such that, on average, 1-3 hydrophobic groups will be linked to each enzyme molecule.

Amino Acid Sequence

A lipolytic enzyme with 1-3 groups may be a variant obtained by modifying the amino acid sequence of a given lipolytic enzyme by recombinant technology using site-directed mutagenesis.

Thiol groups can also be introduced by chemical reaction as described in Duncan et al., (1983) Anal. Biochem.132, 68-73.

The N-terminal amino group may be eliminated by using site-directed mutagenesis to change the N-terminal to glutamine and after expression convert this to pyroglutamate by cyclization (Thiede, B, Lamer S., Mattow J., Siejak F., Dimmler C., Rudel T., Jungblut P R.; rapid communications in Mass spectroscopy Vol 14 (6) pp. 496-502 (2000). A choice for expression of pyroglutamate containing peptide in filamentous fungi, could be to use parts of the signal peptide and N-terminal of the peroxidase from the filamentous fungi *Coprinus cinereus*. This peroxidase has an N-terminal pyroglutamate (Baunsgaard L., Dalboge H., Houen G., Rasmussen E M, Welinder K G:, European journal of Biochemistry vol. 213 (1) 605-611 (1993).

The peroxidase N-terminal and part of the neighboring amino acids can be conferred to the N-terminal of the lipolytic enzyme by standard molecular biological techniques to created a variant with a pyro-glutamic N-terminal.

Lipolytic Enzyme Variant

The lipolytic enzyme variant may be designed to change the number and location of amino or thiol groups by amino acid insertion, deletion and/or substitution involving lysine or cysteine.

A change in the number of lysine residues may be balanced by a change in the number of other charged amino acids may, to keep the isoelectric point fairly unchanged. Thus, lysine may be substituted with another positively charged amino acid (histidine or arginine).

One strategy is to remove some of the lysine residues by substitution or deletion and keep 1-3 lysine residues unchanged. Thus, of the 6 lysine residues in the *Humicola lanuginosa* lipase, one or more of the following may be retained: K24, K98, K233.

Another strategy is to remove all lysine residues in the native lipolytic enzyme by substitution or deletion (and optionally remove the N-terminal amino group) and to introduce one, two or three lysine residues by substitution or insertion at selected positions in the lipid contact zone.

Thus, for a lipolytic enzyme of the Humicola family, existing amino groups may be removed, and 1-3 lysine residues may be introduced at positions corresponding to the following amino acids in the *Humicola lanuginosa* lipase: 14, 15, 17-28, 35-42, 45, 54-65, 80-85, 87-95, 110-116, 119, 144-151, 171-177, 195-209, 213-215, 219, 221-231, 234, 238, 242-251, 257-269, particularly at position 199, 56, 27, 111, 118, 37, 227, 226, 210, 95, 93, 255, 96, 252, 57 or 211.

Similarly, for a fungal cutinase, existing amino groups may be removed and 1-3 lysine residues may be introduced, e.g. by substitutions corresponding to I5K, V158K, D63K, N44K and/or R149K. Examples are I5K+V158K+D63K and N44K+V158K+D63K.

Use of Modified Lipolytic Enzyme

The modified lipolytic enzyme can be used in any known application for such enzymes, e.g. in baking, in detergents or in immobilized form for various processes.

Baking

The modified lipolytic enzyme can be used in the preparation of dough, bread and cakes, e.g. to increase dough stability and dough handling properties, to increase the loaf volume or to improve the elasticity of the bread or cake. Thus, the enzyme can be used in a process for making bread, comprising adding the enzyme to the ingredients of a dough, kneading the dough and baking the dough to make the bread.

This can be done in analogy with U.S. Pat. No. 4,567,046 (Kyowa Hakko), JP-A 60-78529 (QP Corp.), JP-A 62-111629 (QP Corp.), JP-A 63-258528 (QP Corp.), EP 426211 (Unilever) or WO 99/53769 (Novo Nordisk).

Detergent

The lipolytic enzyme (e.g. a lipase) may be used as an additive in a detergent composition. This additive is conveniently formulated as a non-dusting granulate, a stabilized liquid, a slurry or a protected enzyme. The additive may be prepared by methods known in the art.

Lipases tend to exert the best fat removing effect after more than one wash cycle (Gormsen et al., in Proceedings of the 3rd World Conference on Detergents, AOCS press, 1993., pp 198-203).

Immobilized Enzyme

The lipolytic enzyme may be immobilized by methods known in the art, e.g. by adsorption onto a polymer based carrier, by covalent binding to an activated polymer-based carrier (e.g. epoxy or aldehyde) and by granulation, e.g. as described in WO 89/02916, WO 90/15868, WO 95/22606 or WO 99/33964.

The immobilized lipolytic enzyme may be used for interesterification, e.g. of a water-insoluble carboxylic acid ester (such as a triglyceride) with another ester, with a free fatty acid or with an alcohol. The immobilized enzyme can also be used in ester synthesis or in resolution of racemic compounds.

Detergent Composition

The detergent compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

The detergent composition of the invention comprises the lipase of the invention and a surfactant. Additionally, it may optionally comprise a builder, another enzyme, a suds suppresser, a softening agent, a dye-transfer inhibiting agent and other components conventionally used in detergents such as soil-suspending agents, soil-releasing agents, optical brighteners, abrasives, bactericides, tarnish inhibitors, coloring agents, and/or encapsulated or non-encapsulated perfumes.

The detergent composition according to the invention can be in liquid, paste, gels, bars or granular forms. The pH (measured in aqueous solution at use concentration) will usually be neutral or alkaline, e.g. in the range of 7-11, particularly 9-11. Granular compositions according to the present invention can also be in "compact form", i.e. they may have a relatively higher density than conventional granular detergents, i.e. form 550 to 950 g/l.

The lipase of the invention, or optionally another enzyme incorporated in the detergent composition, is normally incorporated in the detergent composition at a level from 0.00001% to 2% of enzyme protein by weight of the composition, particularly at a level from 0.0001% to 1% of enzyme protein by weight of the composition, more particularly at a level from 0.001% to 0.5% of enzyme protein by weight of the composition, even more particularly at a level from 0.01% to 0.2% of enzyme protein by weight of the composition.

The detergent composition of the invention may comprise the lipase in an amount corresponding to 10-50,000 LU per gram of detergent, particularly 20-5,000 LU/g, e.g. 100-1000 LU/g. The detergent may be dissolved in water to produce a wash liquor containing lipolytic enzyme in an amount corresponding to 25-15,000 LU per liter of wash liquor, particularly 100-5000 LU/l, e.g. 300-2000 LU/l. The amount of lipase protein may be 0.001-10 mg per gram of detergent or 0.001-100 mg per liter of wash liquor.

More specifically, the lipase of the invention may be incorporated in the detergent compositions described in WO 97/04079, WO 97/07202, WO 97/41212, PCT/DK WO 98/08939 and WO 97/43375.

Surfactant System

The surfactant system may comprise nonionic, anionic, cationic, ampholytic, and/or zwitterionic surfactants. The surfactant system may comprise a combination of anionic and non-ionic surfactant with 70-100% by weight of anionic surfactant and 0-30% by weight of nonionic, particularly 80-100% of anionic surfactant and 0-20% nonionic or 40-70% anionic and 30-60% non-ionic surfactant.

The surfactant is typically present at a level from 0.1% to 60% by weight, e.g. 1% to 40%, particularly 10-40%. particularly from about 3% to about 20% by weight. Some examples of surfactants are described below.

Anionic Surfactants

Suitable anionic surfactants include alkyl sulfate, alkyl ethoxy sulfate, linear alkyl benzene sulfonate and mixtures of these.

The alkyl sulfate surfactants are water soluble salts or acids of the formula $ROSO_3M$ wherein R particularly is a $C_{10}$-$C_{24}$ hydrocarbyl, particularly an alkyl or hydroxyalkyl having a $C_{10}$-$C_{20}$ alkyl component, more particularly a $C_{12}$-$C_{18}$ alkyl or hydroxyalkyl, and M is H or a cation, e.g., an alkali metal cation (e.g. sodium, potassium, lithium), or ammonium or substituted ammonium.

Alkylbenzene sulfonates are suitable, especially linear (straight-chain) alkyl benzene sulfonates (LAS) wherein the alkyl group particularly contains from 10 to 18 carbon atoms.

Suitable anionic surfactants include alkyl alkoxylated sulfates which are water soluble salts or acids of the formula $RO(A)_mSO_3M$ wherein R is an unsubstituted $C_{10}$-$C_{24}$ alkyl or hydroxyalkyl group having a $C_{10}$-$C_{24}$ alkyl component, particularly a $C_{12}$-$C_{20}$ alkyl or hydroxyalkyl, more particularly $C_{12}$-$C_{18}$ alkyl or hydroxyalkyl, A is an ethoxy or propoxy unit, m is greater than zero, typically between about 0.5 and about 6, more particularly between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl, tri-methyl-ammonium cations and quaternary ammonium cations such as tetramethyl-ammonium and dimethyl piperdinium cations and those derived from alkylamines such as ethylamine, diethylamine, triethylamine, mixtures thereof, and the like.

Other anionic surfactants include salts (including, for example, sodium, potassium, ammonium, and substituted ammonium salts such as mono- di- and triethanolamine salts) of soap, $C_8$-$C_{22}$ primary or secondary alkanesulfonates, $C_8$-$C_{24}$ olefinsulfonates, sulfonated poly-carboxylic acids prepared by sulfonation of the pyrolyzed product of alkaline earth metal citrates.

Nonionic Surfactant

The surfactant may comprise polyalkylene oxide (e.g. polyethylene oxide) condensates of alkyl phenols. The alkyl group may contain from about 6 to about 14 carbon atoms, in a straight chain or branched-chain. The ethylene oxide may be present in an amount equal to from about 2 to about 25 moles per mole of alkyl phenol.

The surfactant may also comprise condensation products of primary and secondary aliphatic alcohols with about 1 to about 25 moles of ethylene oxide. The alkyl chain of the aliphatic alcohol can either be straight or branched, and generally contains from about 8 to about 22 carbon atoms.

Further, the nonionic surfactant may comprise polyethylene oxide condensates of alkyl phenols, condensation products of primary and secondary aliphatic alcohols with from about 1 to about 25 moles of ethylene oxide, alkylpolysaccharides, and mixtures hereof, particularly $C_8$-$C_{14}$ alkyl phenol ethoxylates having from 3 to 15 ethoxy groups and $C_8$-$C_{18}$ alcohol ethoxylates (particularly $C_{10}$ avg.) having from 2 to 10 ethoxy groups, and mixtures thereof.

Examples of nonionic surfactants are alcohol ethoxylate, alcohol phenol ethoxylate, polyhydroxy fatty acid amide, alkyl polyglucoside and mixtures of these.

EXAMPLES

Example 1

Modified Lipases with an Average of 3 Hydrophobic Groups

Modified lipases were prepared by covalently linking tetradecanoyl ($C_{14}$) and hexadecanoyl ($C_{16}$) groups, respectively, to Lipolase (*Humicola lanuginosa* lipase). Each lipase molecule has 7 amino groups (N-terminal+6 lysine residues), and it was estimated that an average of 3 fatty acyl groups were linked to each molecule.

Example 2

Modified Lipases with 3 or 4 Hydrophobic Groups

Two variants of Lipolase were prepared by amino acid substitutions so that the variants had the following amino groups. Other lysine residues were substituted with arginine:

Three amino groups N-terminal and lysine at positions 46 and 98.

Four amino groups: N-terminal and lysine at positions 24, 46 and 98.

Fatty acyl groups (myristoyl and stearoyl, respectively) were linked covalently to the amino groups in each variant.

Example 3

Modified Lipases with 2 Hydrophobic Groups

A variant of Lipolase was prepared by substituting lysine residues with arginine to obtain a lipase variant having two amino groups, at the N-terminal and Lys 24.

Four different modified lipases were produced by linking the following hydrophobic groups to the amino groups in the variant:

Stearoyl $C_{18}H_{37}$—(O—$CH_2$—$CH_2$)$_{100}$ $C_{18}H_{37}$—(O—$CH_2$—$CH_2$)$_{21}$ Arachidoyl A similar modified lipase may be made by linking to palmitoyl groups.

Example 4

Construction of Modified Lipases

Monopods, dipods and tripods are prepared from Lipolase by removing the N-terminal amino group by pyroglutamate cyclization and making variants by amino acid substitutions having lysine at the following positions. Other lysine residues are substituted with arginine:

Monopod: lysine at position 98, 211 or 223.

Dipod: lysine residues at positions 98+233 or 96+255.

Tripod: Lysine residues at positions 24+98+223 or at positions 57+96+252.

Hydrophobic groups (fatty acyl or polypropylene) are linked covalently to the lysine residues in each variant.

Example 5

First-Wash Performance

The two modified lipases were tested as described below, and unmodified Lipolase was tested for comparison.

A number of variants according to the invention were tested in an anionic detergent. The experimental conditions were as follows:

Equipment: Thermostated Terg-o-tometer

Method: 1 cycle wash followed by line drying.

Wash liquor: 1000 ml per beaker

Swatches: 7 (cotton style # 400) swatches (9*9 cm) per beaker.

Stain: Lard coloured with Sudan red (0.75 mg Sudan red/g lard). 250 μl of lard/Sudan red heated to 70° C. is applied to the center of each swatch, followed by line-drying over-night.

Water: 8.4° German hardness (° dH), Ca: Mg=2:1

Detergent: 1.8 g/l commercial detergent (Wisk)

Lipase dosage: as indicated below

Wash time: 20 min.

Temperature: 30° C.

Rinse: 15 minutes in running tap water.

Drying: Overnight at room temperature (~20° C., 30-40% RH).

Evaluation: The reflectance was measured at 460 nm in a reflectometer.

The results are given as ΔR (delta Reflectance)=reflectance of swatches washed in detergent with lipase minus reflectance of swatches washed in detergent without lipase.

Results:

|  | Lipase | Dosage, LU/l | ΔR |
|---|---|---|---|
| Reference | Lipolase | 1329 | 0.3 |
|  |  | 4011 | 0.7 |
| Invention | Lipolase modified with $C_{14}$ | 1617 | 1.9 |
|  |  | 4880 | 5.2 |
|  | Lipolase modified with $C_{16}$ | 1212 | 2.2 |
|  |  | 3658 | 5.5 |

The results clearly demonstrate that the modified lipases have an improved first-wash performance.

Example 6

Baking Tests

A chemically modified lipase was prepared by linking palmitoyl groups to *Humicola lanuginosa* lipase. The amounts of reagents were chosen so as to link an average of 2-3 acyl groups to each lipase molecule.

The chemically modified lipase was compared the unmodified lipase in a traditional European straight dough baking procedure.

The volume and the shape of the rolls were evaluated. Volume was evaluated by simple displacement of 10 rolls, and the shape was evaluated by measuring height/width. The results were as follows

|  | Invention (modified lipase) | Reference (unmodified lipase) |
| --- | --- | --- |
| Lipase dosage, LU/kg flour | 500 | 1000 |
| Volume, ml/g | 6.4 | 6.2 |
| Shape (Height/width) | 0.68 | 0.64 |

The results clearly show that the modified lipase at half the dosage of the reference has improved performance in terms of volume and shape.

The invention claimed is:

1. A method of preparing a dough or a baked product from the dough which comprises adding to the dough a lipolytic enzyme composition comprising lipolytic enzymes modified by covalently linking non-amino acid hydrophobic groups to an amino group, a thiol group, a hydroxyl group or a carboxyl group of the lipolytic enzymes, and wherein said hydrophobic groups are present in said lipolytic enzyme composition on average of two to three hydrophobic groups per lipolytic enzyme.

2. A dough composition comprising a lipolytic enzyme composition comprising lipolytic enzymes modified by covalently linking non-amino acid hydrophobic groups to an amino group, a thiol group, a hydroxyl group or a carboxyl group of the lipolytic enzymes, and wherein said hydrophobic groups are present in said lipolytic enzyme composition on average of two to three hydrophobic groups per lipolytic enzyme.

3. The method of claim 1, wherein the hydrophobic groups of the lipolytic enzyme composition are fatty acyl groups.

4. The method of claim 1, wherein the lipolytic enzymes consist of two or three amino acids having an amino group and wherein said hydrophobic groups are covalently linked to the two or three amino acids.

5. The method of claim 1, wherein the hydrophobic groups are selected from the group consisting of a fatty acyl group, a polyalkoxy and an alkyl-polyalkoxy group.

6. The method of claim 1, wherein the lipolytic enzymes are Humicola lipolytic enzymes.

7. The method of claim 1, wherein the lipolytic enzymes are *Humicola lanuginosa* lipases.

8. The method of claim 1, wherein the lipolytic enzymes are selected from the group consisting of a lipase, a cutinase and a phospholipase.

9. The method of claim 1, wherein a lipolytic enzyme composition comprises lipolytic enzymes modified by covalently linking non-amino acid hydrophobic groups to an amino group of the lipolytic enzymes.

10. The method of claim 1, wherein a lipolytic enzyme composition comprises lipolytic enzymes modified by covalently linking non-amino acid hydrophobic groups to a thiol group of the lipolytic enzymes.

11. The method of claim 1, wherein a lipolytic enzyme composition comprises lipolytic enzymes modified by covalently linking non-amino acid hydrophobic groups to a hydroxyl group of the lipolytic enzymes.

12. The method of claim 1, wherein a lipolytic enzyme composition comprises lipolytic enzymes modified by covalently linking non-amino acid hydrophobic groups to a carboxyl group of the lipolytic enzymes.

* * * * *